United States Patent [19]

Torgerson

[11] Patent Number: 5,019,377
[45] Date of Patent: * May 28, 1991

[54] LOW GLASS TRANSISTION TEMPERATURE ADHESIVE COPOLYMERS FOR USE IN HAIR STYLING PRODUCTS

[75] Inventor: Peter M. Torgerson, Washington Court House, Ohio

[73] Assignee: The Procter & Gamble Company, Cincinnati, Ohio

[*] Notice: The portion of the term of this patent subsequent to Oct. 16, 2007 has been disclaimed.

[21] Appl. No.: 379,516

[22] Filed: Jul. 13, 1989

Related U.S. Application Data

[60] Division of Ser. No. 285,137, Dec. 16, 1988, abandoned, which is a continuation of Ser. No. 131,863, Dec. 11, 1987, abandoned.

[51] Int. Cl.$^5$ .............................................. A61K 7/11
[52] U.S. Cl. ...................................... 424/70; 424/47; 424/71; 424/81
[58] Field of Search ............................ 424/70, 71, 81

[56] References Cited

U.S. PATENT DOCUMENTS

| | | | |
|---|---|---|---|
| 2,816,882 | 12/1957 | Schiller | 526/307.7 |
| 2,834,763 | 5/1958 | Halpern et al. | 526/245 |
| 3,072,536 | 9/1963 | Pye | 424/81 X |
| 3,222,329 | 12/1965 | Grosser et al. | 260/80.5 |
| 3,577,517 | 5/1971 | Kubot et al. | 424/47 |
| 3,743,715 | 7/1973 | Viout et al. | 424/47 |
| 3,907,984 | 9/1975 | Calvert et al. | 424/47 |
| 3,936,513 | 2/1976 | Lorenz et al. | 525/379 |
| 4,012,501 | 3/1977 | Farber | 424/47 |
| 4,030,512 | 6/1977 | Papantoniou et al. | 132/7 |
| 4,067,839 | 1/1978 | Schultz | 526/916 |
| 4,151,333 | 4/1979 | Lenke et al. | 526/307.7 |
| 4,165,367 | 8/1979 | Chakrabarti | 424/47 |
| 4,196,190 | 4/1980 | Gehman et al. | 424/47 |
| 4,223,009 | 9/1980 | Chakrabarti | 44/47 |
| 4,272,511 | 6/1981 | Papantoniou et al. | 424/47 |
| 4,283,384 | 8/1981 | Jacquet et al. | 424/47 |
| 4,373,825 | 2/1983 | Bolich, Jr. et al. | 424/70 |
| 4,387,090 | 6/1983 | Bolich, Jr. | 24/70 |
| 4,548,990 | 10/1985 | Mueller et al. | 526/320 |
| 4,798,721 | 1/1989 | Yahagi et al. | 424/70 |

FOREIGN PATENT DOCUMENTS

| | | | |
|---|---|---|---|
| 1195050 | 6/1965 | Fed. Rep. of Germany | 526/307.7 |
| 60-229909 | 11/1985 | Japan | 526/307.7 |
| 60-250015 | 12/1985 | Japan . | |
| 0833995 | 5/1981 | U.S.S.R. | 526/307.7 |
| 467402 | 6/1937 | United Kingdom | 526/307.7 |
| 764409 | 12/1956 | United Kingdom | 526/307.7 |
| 2155788 | 10/1985 | United Kingdom . | |

OTHER PUBLICATIONS

Technical Leaflet—Luviskol VA grades—12/84.
Technical Leaflet—Luviskol VAP grades—2/84.
Encyclopedia of Polymer Science & Engineering, vol. 7, pp. 531-544, John Wiley and Sons, 1987.
Copending application, Ser. No. 285,137, Torgerson, filed 12/16/88.
Copending application, Ser. No. 131,954, Bolich, Jr. et al., filed 12/11/87.

*Primary Examiner*—Thurman K. Page
*Assistant Examiner*—S. Rucker
*Attorney, Agent, or Firm*—Gretchen R. Hatfield; Steven J. Goldstein; Leonard W. Lewis

[57] ABSTRACT

The present invention relates to low glass transition temperature adhesive copolymers useful in products such as those which provide hair styling hold, e.g., aerosol mousses, shampoos and conditioners. The monomer components in these copolymers are randomly distributed in the copolymer chain, preferably to form a substantially linear chain. At least one of the monomer components is selected from acrylate amides and methacrylate amides; and furthermore at least one of the other monomer components is selected from acrylate esters and methacrylate esters. These copolymers have a single glass transition temperature within the temperature range of from about 0° C. to about 80° C. The present invention further relates to hair styling compositions (e.g., aerosol mousses, shampoos, conditioners) comprising these adhesive copolymers, and to methods for providing styling hold to hair by using an adhesive copolymer or composition of the present invention.

12 Claims, No Drawings

LOW GLASS TRANSITION TEMPERATURE ADHESIVE COPOLYMERS FOR USE IN HAIR STYLING PRODUCTS

This is a division of application Ser. No. 285,137, filed on Dec. 16, 1988, which was a continuation of application Ser. No. 131,863 filed on Dec. 11, 1987, both now abandoned.

BACKGROUND OF THE INVENTION

The present invention relates to low glass transition temperature adhesive copolymers useful in hair-care products to provide hair styling hold, e.g., hair sprays, mousses, shampoos, and conditioners. The present invention further relates to hair styling compositions containing the copolymers of the present invention. In addition, the present invention relates to methods for providing styling hold to hair by utilizing a copolymer or hair styling composition of the present invention.

The desire to have hair retain a particular shape or configuration is one shared by many people, men and women alike. Approaches taken can either involve permanent alteration of the hair or a temporary alteration. The former involves the use of chemical agents to react with the hair in order to achieve the desired effect. This process can be carried out at either room temperature or elevated temperature.

The temporary set given to hair is, as the term indicates, a temporary arrangement which can be removed by water or by shampooing. The materials used to provide the set have generally been resins or gums. The temporary set compositions have taken the form of gels, lotions, and sprays, and, in more recent years, the form of an aerosol foam (i.e., a styling mousse). The compositions are most often applied to hair dampened with water; then combed or spread throughout the hair by other means; followed by letting the hair dry or blow drying the hair.

The set given will vary depending on the materials used. Temporary set hair styling products typically utilize adhesive polymers which are ethanol or water-soluble rigid polymers having glass transition temperatures well above the temperatures experienced in styling hair. Examples of such high glass transition temperature adhesive polymers are found in U.S. Pat. Nos. 3,743,715 to Viout and Papantoniou, issued July 3, 1973; 4,165,367 to Chakrabarti, issued Aug. 21, 1979; and 4,223,009 to Chakrabarti, issued Sept. 16, 1980; the disclosures of all these patents being incorporated herein by reference in their entirety. These adhesive polymers are typically applied to the hair in an ethanol or water solvent, and then set to form rigid welds between hair fibers when the solvent evaporates as the hair dries. These hair fiber welds form the basis for the style hold ability of conventional hair styling products. When these welds are broken, they remain broken unless the appropriate polymer solvent is added to redissolve the adhesive and reform the welds when the hair dries.

In addition, many polymers said to be useful in hair styling products are multi-component polymers which combine three, four, and even more monomers into the polymer chains. Frequently, one of the monomer components is vinyl pyrrolidone. Examples of such complex polymer systems are found in U.S. Pat. Nos. 3,222,329 to Grosser, et al., issued Dec. 7, 1965; 3,577,517 to Kubot, et al., issued May 4, 1971; 4,012,501 to Farber, issued Mar. 15, 1977; and 4,272,511 to Papantoniou and Mondet, issued June 9, 1981; the disclosures of all these patents being incorporated herein by reference in their entirety.

Other polymers said to be useful for hair styling compositions have been disclosed, such as block polymers. These block polymers have two or more glass transition temperatures. Examples of such block polymer systems are found in U.S. Pat. Nos. 3,907,984 to Calvert, et al., issued Sept. 23, 1975; 4,030,512 to Papantoniou, et al., issued June 21, 1977; and 4,283,384 to Jacquet, et al., issued Aug. 11, 1981; the disclosures of all these patents being incorporated herein by reference in their entirety.

Notwithstanding the great effort already put forth to identify these adhesive polymers for use in temporary set hair styling products, there remains a continuing need to identify new polymers which are useful to provide temporary set and other desirable properties to hair. The copolymers of the present invention are copolymers containing two or more selected monomer components randomly distributed in the copolymer chain, and having a single glass transition temperature within the temperature range of from about 0° C. to about 80° C. These copolymers have several properties which make them superior to previously disclosed hair styling polymers for application to hair.

Thus, an object of the present invention is to provide low glass transition temperature adhesive copolymers useful for providing temporary set style hold to hair. Another object is to provide adhesive copolymers that provide this temporary set style hold while remaining pliable on the hair. A further object is to provide adhesive copolymers which lengthen the time such temporary set style hold is perceived to be acceptable. Also, an object is to provide adhesive copolymers which provide good temporary set hair style retention while allowing the perception of continued naturalness such as good hair movement and good hair feel. In addition, an object is to provide polymers which do not make hair feel stiff or sticky. An object of the present invention is also to provide adhesive copolymers which give body and/or fullness to hair, and/or which give the ability to provide lift to hair, and/or which increase hair volume. Another object is to provide adhesive copolymers which are easy to synthesize and utilize in hair styling compositions. Finally, an object of the present invention is to provide superior hair styling compositions comprising the adhesive copolymers of the present invention; and to provide an improved method for styling hair by utilizing an adhesive copolymer or hair styling composition of the present invention.

These and other objects of the present invention will become readily apparent from the detailed description which follows.

All percentages and ratios used herein are by weight unless otherwise specified.

SUMMARY OF THE INVENTION

The present invention relates to low glass transition temperature adhesive copolymers which are particularly useful in hair styling products. These copolymers comprise two or more monomers which are randomly distributed in a copolymer chain (preferably a substantially linear copolymer chain) such that the copolymer has a single glass transition within the temperature range of from about 0° C. to about 80° C. At least one of the monomer components is selected from acrylate amides or methacrylate amides; and furthermore at least one of the other monomer components is selected from acrylate esters or methacrylate esters.

The present invention further relates to hair styling compositions comprising from about 0.1% to about 20% of at least one low glass transition temperature adhesive copolymer of the present invention, and from about 80% to about 99.9% of a carrier suitable for applying the adhesive copolymer to hair.

Finally, the present invention relates to methods for providing style hold to hair, said method comprising applying to hair in need of style hold an effective amount of a low glass transition temperature adhesive copolymer of the present invention.

DETAILED DESCRIPTION OF THE INVENTION

I. Hair Styling Compositions (a) Low Glass Transition Temperature Adhesive Copolymers:

Generally, the low glass transition temperature adhesive copolymers of the present invention are random copolymers having the general structure:

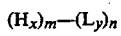

$$(H_x)_m - (L_y)_n$$

wherein H is one or more monomer components having homopolymers with relatively high glass transition temperatures, with at least one H monomer component being selected from acrylate amides or methacrylate amides; L is one or more monomer components having homopolymers with relatively low glass transition temperatures, with at least one L monomer component being selected from acrylate ester or methacrylate esters; x is the number of different H monomer components present in the copolymer chain, with x being an integer of 1 or greater (preferably x is 1 or 2; most preferably x is 1); y is the number of different L monomer components present in the copolymer chain, with y being an integer of 1 or greater (preferably y is 1 or 2; most preferably y is 2); the sum of $x+y$ is 2 or greater (preferred is $x+y$ being 2 or 3); and m:n is the weight ratio of the H monomer components to L monomer components, and is generally within the range of from about 20:1 to about 1:20 (preferably from about 10:1 to about 1:10).

Furthermore, a low glass transition temperature adhesive copolymer of the present invention comprises the hereinbefore described monomer components randomly distributed in a copolymer chain (preferably a substantially linear copolymer chain, i.e., having little or no cross-linking or branching of the copolymer chains) such that the copolymer has a single glass transition temperature within the temperature range of from about 0° C. to about 80° C., preferably within the temperature range of from about 20° C. to about 75° C., and most preferably from about 30° C. to about 60° C.

The H and L monomer components to be used for synthesizing the copolymers of the present invention are readily chosen based on the the glass transition temperature of a homopolymer of the monomer and hydrophobicity/hydrophilicity of the monomer. Since the copolymers of the present invention have two or more component monomers, one or more of the component monomers will be such that it forms a homopolymer having a glass transition temperature above the temperature desired for the copolymer to be synthesized (i.e., the H monomer components); and one or more of the other component monomers will be such that it forms a homopolymer having a glass transition temperature below the desired glass transition temperature (i.e., the L monomer components). Combining these monomer components randomly in various weight ratios gives copolymers which have single glass transition temperatures between the higher and lower glass transition temperatures for the homopolymers of the monomers utilized. Monomers which may be utilized in the present copolymers and which have glass transition temperatures for their homopolymers above and below the desired single glass transition temperature range for the copolymers of the present invention are known, certain of which having been disclosed, for example, in U.S. Pat. No. 3,907,984 to Calvert, et al., issued Sept. 23, 1975 and incorporated herein by reference in its entirety.

In addition, if a relatively hydrophobic copolymer is desired (e.g., for use in shampoos and conditioners), relatively hydropholic monomers are utilized; and if a relatively hydrophilic copolymer is desired (e.g., for use in mousses), relatively hydrophilic monomers are utilized. Thus, simple manipulation of the weight ratios of the monomers during synthesis of the copolymers and appropriate selection of the relative hydrophilicity/hydrophobicity of the monomers utilized, followed by analysis of the resulting copolymers' single glass transition temperatures, permits easy synthesis of copolymers useful in the present invention having the desired combination of single glass transition temperature and solubility.

Preferred is all L monomer components being selected from acrylate esters and/or methacrylate esters. Preferred acrylate esters and methacrylate esters are the $C_1-C_{15}$ esters of acrylate and methacrylate, for example, methylacrylate, ethylacrylate, propylacrylate, butylacrylate, n-butylmethacrylate, iso-butylmethacrylate, methylmethacrylate, ethylmethacrylate, 2-ethylhexylacrylate, 2-ethylhexylmethacrylate, laurylacrylate, laurylmethacrylate, and methoxyethylacrylate. More preferred L are iso-butylmethacrylate, 2-ethylhexylmethacrylate and methoxyethylacrylate.

Also preferred is all H monomer components being selected from acrylate amides and/or methacrylate amides. Preferred acrylate amides and methacrylate amides are unsubstituted or substituted with one or two $C_1-C_5$ alkyl groups (i.e., having the general structure $CH_2=CR(CONR^1R^2)$, wherein R is H or $CH_3$, $R^1$ is H or $C_1-C_5$ alkyl, and $R^2$ is H or $C_1-C_5$ alkyl). Examples include acrylamide, methacrylamide, N-methylacrylamide, N,N-dimethylmethacrylamide, N-isopropylacrylamide, and N,N-dimethylacrylamide. More preferred H monomer components are acrylamide, methacrylamide, N-isopropylacrylamide, and especially N,N-dimethylacrylamide.

Preferably, for the copolymers of the present invention, one monomer component is relatively hydrophilic. Preferred relatively hydrophilic monomer component for use in the copolymers of the present invention are the acrylate amides and methacrylate amides, for example, acrylamide, methacrylamide, N-isopropylacrylamide, and especially N,N-dimethylacrylamide. Acrylic acid and methacrylic acid, and their salts, may also be utilized if the adhesive polymers containing such acids or salts are prepared and formulated to have a glass transition temperature within the range of from about 0° C. to about 80° C. (keeping in mind that pH and degree of neutralization of these component monomers will affect the polymer's glass transition temperature). Furthermore, these acid and salt monomer components are especially not preferred for use in formulations containing cationic materials such as are typically employed in hair conditioner formulations. Preferred monomer components which have relatively less hydrophilicity are the acrylate esters and methacrylate esters, for example, methylacrylate, ethylacrylate, propylacrylate, butylacrylate, n-butylmethacrylate, iso-butylmethacrylate, methylmethacrylate, ethylmethacrylate, 2-ethylhexylacrylate, 2-ethylhexylmethacrylate, laurylacrylate, laurylmethacrylate, and methoxyethylacrylate.

The most preferred low glass transition temperature adhesive copolymers of the present invention are random copolymers comprising N,N-dimethylacrylamide and two or more acrylate or methacrylate esters having the general structure:

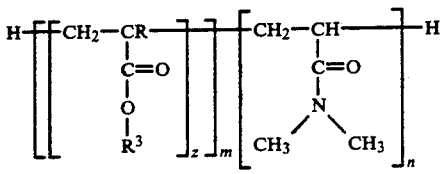

wherein z is the number of different acrylate and methacrylate esters monomer components present in the copolymer chain, with z being an integer of one or greater (preferably z=1 or 2); m:n is the weight ratio of the other monomer components to the N,N-dimethylacrylamide monomer component, and the ratio of m:n is generally within the range of from about 20:1 to about 1:20 (preferably from about 10:1 to about 1:10); R is selected from hydrogen or methyl; and $R^3$ is $C_1$-$C_{15}$ alkyl (preferably $C_1$-$C_{10}$ alkyl). More preferred $R^3$ groups are selected from methyl, ethyl, n-propyl, iso-propyl, n-butyl, sec-butyl, iso-butyl, tert-butyl, pentyl, 2-ethylhexyl, and —$(CH_2)_2OCH_3$; with most preferred $R^3$ being n-butyl, iso-butyl, 2-ethylhexyl, and —$(CH_2)_2OCH_3$.

The term "alkyl", as used herein, means a straight, branched or cyclic carbon-containing chain which is saturated or unsaturated (e.g., one double bond; one triple bond), and which is unsubstituted or substituted with one or more (preferably one) substituent selected from hydroxy, methoxy, ethoxy, propoxy, butoxy, and halogen. Preferred are straight or branched chain, saturated alkyl groups which are unsubstituted or monosubstituted with methoxy.

Representative examples of adhesive copolymers of the present invention are: ethylacrylate/N,N-dimethylacrylamide (60:40; glass transition temperature=29° C.); butylmethacrylate/N,N-dimethylacrylamide (80:20; glass transition temperature=41° C.); methoxyethylacrylate/N,N-dimethylacrylamide (49:51; glass transition temperature=35° C.); methoxyethylacrylate/N,N/-dimethylacrylamide (29:71; glass transition temperature=75° C.); isobutylmethacrylate/2-ethylhexylmethacrylate/N,N-dimethylacrylamide (60:30:10; glass transition temperature=38° C.); isobutylmethacrylate/2-ethylhexylmethacrylate/N,N-dimethylacrylamide (30:40:30; glass transition temperature=44° C.); butylmethacrylate/ethylacrylate/N,N-dimethylacrylamide; butylmethacrylate/methoxyethylacrylate/N,N-dimethylacrylamide; butylacrylate/methoxyethylacrylate/N,N-dimethylacrylamide; butylacrylate/butylmethacrylate/N,N-dimethylacrylamide; and butylacrylate/butylmethacrylate/methoxyethylacrylate/N,N-dimethylacrylamide. Preferred copolymers of the present invention are: methoxyethylacrylate/N,N-dimethylacrylamide (49:51) and methoxyethylacrylate/N,N-dimethylacrylamide (29:71), especially for use in mousse compositions; and isobutylmethacrylate/2-ethylhexylmethacrylate/N,N-dimethylacrylamide (60:30:10 and 30:40:30), especially for use in cream rinse compositions.

Preferably the adhesive copolymers of the present invention have a number average molecular weight within the range of from about 10,000 to about 1,000,000, more preferably within the range of from about 10,000 to about 250,000, and most preferably from about 25,000 to about 100,000. It is further preferred that the adhesive copolymers of the present invention have a molecular weight polydispersity (i.e., the ratio of the weight average molecular weight over the number average molecular weight) of about 2.5 or less, preferably from about 2.5 to about 1.0. The adhesive copolymers of the present invention also preferably have an elastic modulus greater than about $10^7$ dynes/cm$^2$, more preferably from about $10^7$ to about $10^{10}$ dynes/cm$^2$, below the copolymer's glass transition temperature. Finally, for use in mousse compositions, it is desirable that the adhesive copolymers of the present invention be soluble in water and/or alcohol; and for use in shampoo and conditioner compositions, it is desirable that the adhesive copolymers of the present invention be essentially insoluble in water and aqueous shampoo and conditioner surfactant systems.

Analytical methods for analysis of the copolymers of the present invention for their glass transition temperature, number-average molecular weights, molecular weight polydispersity, and elastic modulus are well known in the art. For example, these properties of copolymers and analytical methods are described in more detail in Rosen, *Fundamental Principles of Polymeric Materials* (John Wiley & Son, Inc.; New York; 1982), the disclosures of which are incorporated herein by reference in their entirety.

Synthesis methods for preparing random copolymers having substantially linear chains are well known in the art, for example, U.S. Pat. Nos. 3,222,329 to Grosser, et al., issued Dec. 7, 1965; 3,577,517 to Kubot, et al., issued May 4, 1971; 4,272,511 to Papantoniou and Mondet, issued June 9, 1981; and 4,012,501 to Farber, issued Mar. 15, 1977; the disclosures of all these patents being incorporated herein by reference in their entirely. Preferably, the copolymers of the present invention are prepared by utilizing free radical polymerization techniques. Typically, such free radical polymerization techniques use either UV wavelength light or chemicals which generate free radicals to initiate the polymerization reaction. Representative procedures for synthesizing low glass transition temperature adhesive copolymers of the present invention are provided in the examples hereinafter.

It is to be noted that while the adhesive copolymers of the present invention are intended primarily for use in the hair styling compositions and methods of the present invention, these copolymers can have a variety of other uses. For example, these copolymers may be utilized in skin care products such as a film forming body milk, skin cream, skin lotion, or beauty mask; in fingernail lacquer; and as binders for electronic cores, coatings, textile sizes, paints, adhesives, and similar uses.

The hair styling compositions of the present invention typically comprise from about 1% to about 20% of a low glass transition temperature adhesive copolymer of the present invention, preferably from about 0.1% to about 10%, and most preferably from about 1% to about 5%.

(b) Carriers Suitable for Applying Adhesive Polymers to Hair

In addition to the low glass transition temperature adhesive copolymers as described hereinbefore, the hair styling compositions of the present invention essentially contain a carrier suitable for applying the adhesive copolymer to hair. The term "carriers suitable for applying the adhesive copolymer to hair", as used herein, means one or more compatible solid or liquid diluents which are suitable for administration to the hair of a human or lower animal. The term "compatible", as used herein, means that the components of the carrier are capable of being commingled with the adhesive copolymer of the present invention, and with each other, in a manner such that there is no interaction which would substantially reduce the ability of the hair styling compositions to provide temporary set hold to hair under ordinary use situation. These carriers must, of course, be of sufficiently high purity and sufficiently low toxicity to render them suitable for administration to the hair of the human or lower animal to which they are being applied.

The choice of the carriers to be used in conjunction with the adhesive copolymers of the present compositions is basically determined by the form the hair styling composition is to take (e.g., lotion, cream, paste, gel, pump spray, pressurized aerosol spray, pressurized aerosol mousse, etc.) and the intended use of the hair styling composition (e.g., shampoo, conditioner, hair spray, hair mousse). Carriers suitable for applying the adhesive copolymer to hair are well known in the art; and their selection can be made without difficulty by a person skilled in the art. For example, carriers which may be selected for use in the hair styling compositions of the present invention are described in more detail in U.S. Pat. Nos. 3,577,517, to Kubot et al, issued May 4, 1971; 3,907,984, to Calvert et al, issued Sept. 23, 1975; 4,012,501, to Farber, issued Mar. 15, 1977; 4,223,009, to Chakrabarti, issued Sept. 16, 1980; and 4,283,384, to Jacquet et al, issued Aug. 11, 1981; the disclosures of all these patents being incorporated herein by reference in their entirety.

The hair styling compositions of the present invention typically comprise water (preferably distilled or deionized), or a water-alcohol mixture (typically in a water:alcohol ratio within the range of from about 20:1 to about 1:2), as part of the carrier at a level of from about 50% to about 99.9%, preferably from about 65% to about 99%, and more preferably from about 80% to about 99%, of the total hair styling composition. One of the preferred hair styling compositions of the present invention are pressurized aerosol mousses which essentially comprise water or a water-alcohol mixture.

Other carrier components useful in the hair styling compositions of the present invention are suitable for rendering such compositions more acceptable. These include conventional additives such as opacifiers, colorants, perfumes, UV absorbers, preservatives, medicaments, suds boosters or depressants, penetrants, lustrants, deodorants, and the like. Generally, these carriers comprise conventional additives found in hair setting lotions, in hair treating lotions, in hair styling creams or gels, hair treating shampoos, and conditioners, hair setting lotions, hair restructuring agents, hair treating lotions or hair lacquer compositions. Such carriers are described in more detail in U.S. Pat. Nos. 4,223,009, to Chakrabarti, issued Sept. 16, 1980, and in 4,283,384, to Jacquet et al, issued Aug. 11, 1981, the disclosures of both these patents being incorporated by reference herein in their entirety.

Carrier components particularly suited for certain types of hair styling compositions are described in detail as follows:

(i) Mousse Compositions

An essential carrier component of the preferred hair styling mousses of the present invention is a propellant. This agent is responsible for expelling the material from the container and forming the mousse character of the composition as applied to the hair. The propellant gas can be any liquifiable gas conventionally used for aerosol containers. Preferably the density of the propellant is less than one so that pure propellant is not emitted from the container. Examples of materials which are suitable for use as propellants are trichlorofluoromethane, dichlorodifluoromethane, dichlorotetrafluoroethane, monochlorodifluoromethane, trichlorotrifluoroethane, dimethyl ether, propane, n-butane and isobutane, use singly or admixed. The hydrocarbons, particularly isobutane, used singly or admixed with other hydrocarbons, are preferred due to their densities being less than one.

The amount of the propellant gas is governed by normal factors well known in the aerosol art. For mousses the level of propellant is generally from about 5% to about 20%, preferably from about 7% to about 15% of the total composition. If a propellant such as dimethylether utilizes a vapor pressure suppressant, (e.g., trichloroethane or dichloromethane), the amount of the suppressant is included as part of the propellant.

Other carriers for pressurized aerosol mousses (which may also be utilized in non-mousse compositions as described in detail hereinafter) are well known to those skilled in the art, e.g., emulsifiers such as anionics (e.g., sodium alkyl sulfate), and nonionics (amine oxides); preservatives such as benzyl alcohol, methyl paraben, propyl paraben and imidazolidinyl urea; cationic emulsifiers/conditioners such as cetyl trimethyl ammonium chloride, stearyldimethyl benzyl ammonium chloride, and di(partially hydrogenated tallow) dimethylammonium chloride; thickeners and viscosity modifiers such as a diethanolamide of a long chain fatty acid; block copolymers of ethylene oxide and propylene oxide such as Pluronic F88 offered by BASF Wyandotte, fatty alcohols such as cetearyl alcohol, sodium chloride, sodium sulfate, and ethyl alcohol; pH adjusting agent such as citric acid, succinic acid, sodium hydroxide, and triethanolamine; coloring agents such as any of the FD&C or D&C dyes; hair oxidizing (bleaching) agents such as hydrogen peroxide, perboric salts and persulfate salts; hair reducing agents such as the thioglycolates; perfume oils; chelating agents such as ethylenediamine tetracetic acid; and, among many other agents, copolymer plasticizing agents such as glycerine. These carrier materials other than the propellant gas, when present in the mousse compositions, are generally used individually at a level of from about 0.01% to about 10%, preferably from about 0.5% to about 5%, by weight of the total composition.

Another type of carrier component useful in the mousse compositions of the present invention is silicone-containing agents such as silicone gums, silicone fluids, and mixtures of silicone gums and silicone fluids. References disclosing silicone gums (which generally may be described as high molecular weight polydiorganosiloxanes having a molecular weight of from about 200,000 to about 1,000,000) include U.S. Pat. No. 4,152,416, issued May 1, 1979 to Spitzer, et al.; *Silicon Compounds*, distributed by Petrarch Systems; Noll, *Chemistry and Technology of Silicones*, New York: Academic Press 1968; and General Electric Silicone Rubber Product Data Sheets SE 30, SE 33, SE 54, and SE 76; the disclosures of all these references being incorporated herein by reference in their entirely. Specific examples include polydimethylsiloxane, (polydimethylsiloxane) (methylvinylsiloxane) copolymer, and poly(-dimethylsiloxane) (diphenyl) (methylvinylsiloxane) copolymer, and mixtures thereof.

Silicone fluids are generally either a polyalkyl siloxane, a polyaryl siloxane, a polyalkylaryl siloxane, or a polyether siloxane copolymer. Silicone fluids preferably have a viscosity of from about 5 to about 10,000 centistokes, more preferably from about 100 to about 1,000 centistokes, at 25° C. The silicone-containing agents, when present in the compositions of the present invention, are generally used individually at a level of from about 0.05% to about 6%, preferably from about 0.1% to about 4%, and more preferably from about 0.1% to about 3%, by weight of the total composition.

The method of preparing a hair styling composition of the present invention follows conventional procedures for the form of the composition desired. For example, the method of preparing an aerosol mousse composition of the present invention follows conventional aerosol filling procedures. For example, the water soluble or dispersible materials are mixed with water to form a "concentrate". This concentrate, in an appropriate amount, is placed into an aerosol container. The container is then fitted with a valve, subjected to a vacuum to rid the container of air, and sealed with the valve "crimped" in place. The propellant is then filled into the container through the valve.

(ii) Cream Rinse and Shampoo Compositions

Volatile diluents are useful in the cream rinse and shampoo compositions of the present invention. These volatile diluents can be hydrocarbons, esters, ethers, amines, alkyl alcohols, silicon derivatives, or mixtures thereof and have a boiling point in the range of from about 99° C. to about 260° C. and have a solubility in water of less than about 0.2%. Preferably the volatile diluent is selected from the group of alkyl alcohols, silicon derivatives, and mixtures thereof. The hydrocarbons may be either straight or branched chain and may contain from about 10 to about 16, preferably from about 12 to about 16 carbon atoms. Examples of suitable hydrocarbons are decane, dodecane, decene, tridecane and mixtures thereof. Also useful are the terpenes such as orange and lemon terpenes. Useful alkyl alcohols can be saturated or unsaturated and branched or straight chain. Preferred alkyl alcohols include linalool and decyl alcohol. The volatile silicon derivatives useful in the compositions of the present invention may be either a cyclic or a linear polydialkylsiloxane, linear siloxy compounds or silane.

The number of silicon atoms in the cyclic silicones is preferably from about 3 to about 7, more preferably about 3 to about 5. The general formula for such silicones is:

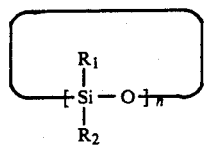

wherein $R_1$ and $R_2$ are independently selected from $C_1$ to $C_8$ alkyl, aryl or alkylaryl and wherein $n=3-7$.

The linear polyorgano siloxanes have from about 2 to 7 silicon atoms and have the general formula:

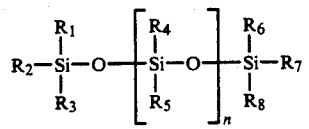

wherein $R_1$, $R_2$, $R_3$, $R_4$, $R_5$, $R_6$, $R_7$, and $R_8$ can independently be saturated or unsaturated $C_1$-$C_8$ alkyl, aryl, alkyl aryl, hydroxyalkyl, amino alkyl or alkyl siloxy, and wherein $n=0-5$.

Linear siloxy compounds have the general formula:

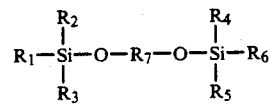

wherein $R_1$, $R_2$, $R_3$, $R_4$, $R_5$ and $R_6$ are independently selected from saturated or unsaturated $C_1$ to $C_7$ alkyl, aryl and alkyl aryl and $R_7$ is $C_1$ to $C_4$ alkylene.

Silane compounds have the general formula:

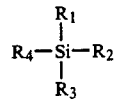

wherein $R_1$, $R_2$, $R_3$, and $R_4$ can independently be selected from $C_1$-$C_8$ alkyl, aryl, alkyl aryl, hydroxy alkyl and alkylsiloxy.

Silicones of the above type, both cyclic and linear, are offered by Dow Corning Corporation, (e.g., Dow Corning 344, 345 and 200 fluids), Union Carbide, (e.g., Silicone 7202 and Silicone 7158), and Stauffer Chemical, (e.g., SWS-03314).

The linear volatile silicones generally have viscosities of less than about 5 centistokes at 25° C. while the cyclic materials have viscosities less than about 10 centistokes. "Volatile" means that the material has a measurable vapor pressure.

A description of volatile silicones is found in Todd and Byers, "Volatile Silicone Fluids for Cosmetics", Cosmetics and Toiletries, Vol. 91, January, 1976, pp. 27-32, and also in Silicon Compounds, pages 253-295, distributed by Petrarch Chemicals, both of which are incorporated herein by reference.

Optionally, certain water-insoluble non-volatile co-solvents can be added at low levels, i.e., less than about 10%, to replace the equivalent amount of the volatile diluents. These co-solvents help to dissolve the adhesive copolymer. Preferred co-solvents include liquid alcohols and liquid fatty acids, such as isocetyl alcohol and olelyl alcohol.

In order to form the styling agent, the adhesive copolymer and the volatile diluent are combined in a weight ratio of from about 1:20 to about 5:1, preferably from about 1:10 to about 1:1 and most preferably from about 1:4 to about 2:3, the resulting styling agents have an average particle diameter of from about 0.5 to about 100 microns, preferably from about 1 micron to about 25 microns.

The hair styling shampoo and conditioner compositions of the present invention contain an adhesive copolymer as described above along with a carrier suitable for applying the styling agent to hair such that these compositions have two or more phases. At least one phase contains the adhesive copolymer and another contains the carrier. Other phases can contain, for example, pearlizing agents such as ethylene glycol distearate or $TiO_2$ coated mica which impart aesthetic benefits to the composition.

The rinse-off hair styling compositions of the present invention typically comprise water (preferably distilled or deionized), or a water-alcohol mixture (typically in a water:alcohol ratio within the range of from about 20:1 to about 1:2), as part of the carrier. The carrier is present at a level of from about 75% to about 99.5%, preferably from about 85% to about 99%, and more preferably from about 90% to about 99%, of the total hair styling composition.

Compositions of this invention formulated in a shampoo form. The shampoos typically comprise from about 1% to about 25% of the adhesive copolymer; from about 5% to about 60% of a synthetic surfactant; and the balance water. Suitable surfactants which have been fully described above include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauroyl sulfate, triethanolamine lauroyl sulfate, triethanolamine lauroyl sulfate, monoethanolamine cocoyl sulfate, monoethanolamine lauroyl sulfate, sodium tridecyl benzene sulfonate and sodium dodecyl benzene sulfonate.

These shampoos can contain a variety of nonessential optional components. Such conventional optional ingredients are well known to those skilled in the art, e.g., preservatives, such as benzyl alcohol, ethyl paraben, propyl paraben and imidazolidinyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; thickeners and viscosity modifiers such as diethanolamide of a long-chain fatty acid (e.g., PEG 3 lauramide), block polymers of ethylene oxide and propylene oxide, sodium chloride, sodium sulfate, polyvinyl alcohol, ethyl alcohol and water-soluble polymers such as xanthan gum, hydroxyethyl cellulose, guar gum and starch; pH adjusting agents, such as citric acid, succinic acid, phosphoric acid, sodium hydroxide, sodium carbonate; perfumes; dyes; and, sequestering agents, such as disodium ethylenediamine tetraacetate. Such agents generally are used individually at a level of from about 0.01% to about 10%, preferably from about 0.5% to about 5.0% by weight of the composition.

Where the hair styling compositions are conditioner compositions, preferred optional components include gel vehicle materials. The vehicle preferably comprises two essential components: a lipid vehicle material and generally a cationic surfactant vehicle material. Such gel-type vehicles are generally described in the following documents, all incorporated by reference herein: Barry, "The Self Bodying Action of the Mixed Emulsifier Sodium Dodecyl Sulfate/Cetyl Alcohol", 28 *J. of Colloid and Interface Science* 82–91 (1968); Barry, et al., "The Self-Bodying Action of Alkyltrimethylammonium Bromides/Cetostearyl Alcohol Mixed Emulsifiers; Influence of Quaternary Chain Length", 35 *J. Colloid and Interface Science* 689–708 (1971); and Barry, et al., "Rheology of Systems Containing Cetomacrogol 1000-Cetostearyl Alcohol, I. Self Bodying Action", 38 *J. of Colloid and Interface Science* 616–625 (1972).

Lipid vehicle materials include naturally or synthetically-derived acids, acid derivatives, alcohols, esters, ethers, ketones, and amides with carbon chains of from 12 to 22, preferably from 16 to 18, carbon atoms in length. Fatty alcohols and fatty esters are preferred; fatty alcohols are particularly preferred.

Lipid vehicle materials among those useful herein are disclosed in *Bailey's Industrial Oil and Fat Products*, (3rd edition, D. Swern, ed. 1979) (incorporated by reference herein). Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et al., issued May 26, 1981; British Specification No. 1,532,585, published Nov. 15, 1978; and Fukushima, et al., "The Effect of Cetostearyl Alcohol in Cosmetic Emulsions", 98 *Cosmetics & Toiletries* 89–102 (1983). Fatty esters included among those useful herein are disclosed in U.S. Pat. No. 3,341,465, Kaufman, et al., issued Sept. 12, 1976 (incorporated by reference herein).

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

The hair styling compositions of the present invention typically comprise from about 80% to about 99.9% of a carrier suitable for applying the adhesive copolymer to hair, preferably from about 90% to about 99%, and most preferably from about 95% to about 99%.

II. Methods for Providing Styling Hold to Hair

Another aspect of the present invention is methods for providing temporary set style hold to hair. Such methods comprise applying to the hair in need of style hold an effective amount of low glass transition temperature adhesive copolymer or hair styling composition of the present invention.

The procedure for applying the adhesive copolymer to the hair will vary according to the form of the hair styling composition being utilized. For example, hair styling compositions in the form of a shampoo or conditioner lotion are typically applied to the hair when wet, with the hair then being rinsed and dried. Hair styling compositions in the form pressurized aerosol sprays typically are sprayed over the dry hair, and then combed or brushed throughout the hair to provide the styling hold. The preferred mousse compositions are typically applied to damp hair, worked through the hair with the fingers or a hair styling implement, and then the hair is rinsed out or let dry (or is blown dry). An effective amount of the adhesive copolymer or composition of the present invention is considered to be an amount sufficient to provide the degree of styling hold desired by the user.

The following examples further describe and demonstrate the preferred embodiments within the scope of the present invention. The examples are given solely for the purpose of illustration and are not to be construed as limitation of the present invention as many variations thereof are possible without departing from spirit and scope.

EXAMPLE I

Synthesis of methoxyethylacrylate/N,N-dimethylacrylamide 50:50

A 50:50 (weight percent) methoxyethylacrylate/N,N-dimethylacrylamide copolymer is prepared as follows. Equal amounts of N,N-dimethylacrylamide and methoxyethylacrylate are weighed out and added to a three neck flask fitted with an argon sparge, mechanical stirrer and condenser. Toluene is then added to the flask to get a final monomer concentration of 20.0 weight percent. The reaction flask is placed in a 60° C. water bath and the reaction mixture is sparged with argon for two hours while stirring. After two hours, azobisisobutyronitrile ("AIBN") is added to the reaction flask in an amount sufficient to get a final initiator concentration of 0.05 weight percent. The reaction is then stirred for two hours, after which time the reaction flask is removed from the water bath and the reaction mixture is poured into a container of hexane to precipitate the copolymer. The copolymer is then removed from the hexane, placed in a polyethylene tray, and dried in a vacuum oven at 30° C. In order to remove any residual monomer, the dried copolymer is dissolved in toluene, reprecipitated in hexane, and then dried again in a vacuum oven.

The resulting copolymer is determined to have a monomer content in a weight ratio of 49:51 (methoxyethylacrylate/N,N-dimethylacrylamide). The glass transition temperature of this copolymer is 35° C. as determined by heat capacity change as measured by a differential scanning calorimeter ("DSC"; Perkin-Elmer Instruments Model #DSC-2. Temperature calibration is effected using the melting point of Indium as a reference temperature. Observed glass transition temperatures are corrected for the effect of temperature scan rate). Number average molecular weight=50,200 (determined by size exclusion chromatography); weight average molecular weight=109,900 (determined by size exclusion chromatography); molecular weight polydispersity=2.19.

A methoxyethylacrylate/N,N-dimethylacrylamide copolymer having monomer content in a weight ratio of 29:71 is prepared by following essentially the same procedure, except that the ethoxyethylacrylate and N,N-dimethylacrylamide are reacted in a weight ratio of 30:70. The glass transition temperature is 75° C. as determined by heat capacity change as measured by a DSC. Number average molecular weight=44,000 (determined by size exclusion chromatography); weight average molecular weight=86,500 (determined by size exclusion chromatography); molecular weight polydispersity=1.97.

A butylmethacrylate/N,N-dimethylacrylamide copolymer having monomer content in a weight ratio of 80:20 is also prepared by following essentially the same procedure, except that butylmethacrylate and N,N-dimethylacrylamide are reacted in a weight ratio of 80:20. The glass transition temperature is calculated to be approximately 30° C.

EXAMPLE II

Mousse Composition

| Component | Weight % |
|---|---|
| Distilled water | 91.35 |
| Hydrocarbon propellant A-46[1] | 5.00 |
| MEAc/DMA (71%)[2] | 3.00 |
| Alkyl dimethyl amine oxide[3] | 0.25 |
| Glydant preservative[4] | 0.20 |
| EDTA | 0.10 |
| Fragrance | 0.10 |

[1] Propane/isobutane/n-butane (20%/78%/2%) offered by Phillips Petroleum Company
[2] Methoxyethylacrylate/N,N-dimethylacrylamide (29:71) which is prepared as in Example 1 hereinbefore
[3] Cocamine oxide
[4] Offered by Glyco Chemical Company Applying this mousse composition to a person's damp hair and distributing the composition throughout the hair with the fingers, followed by warm air blow drying the hair, provides long lasting styling hold to the treated hair without making the hair feel sticky or stiff.

EXAMPLE III

Mousse Composition

| Component | Weight % |
|---|---|
| Distilled water | 91.64 |
| Hydrocarbon propellant A-46[1] | 5.00 |
| MEAc/DMA (71%)[2] | 2.85 |
| Alkyl dimethyl amine oxide[3] | 0.24 |
| Glydant preservative[4] | 0.18 |
| Fragrance | 0.09 |

[1] Propane/isobutane/n-butane (20%/78%/2%) offered by Phillips Petroleum Company
[2] Methoxyethylacrylate/N,N-dimethylacrylamide (29:71) which is prepared as in Example 1 hereinbefore
[3] Cocamine oxide
[4] Offered by Glyco Chemical Company Applying this mousse composition to a person's damp hair and distributing the composition throughout the hair with a brush, followed by warm air blow drying the hair, provides long lasting styling hold to the treated hair without making the hair feel sticky or stiff.

EXAMPLE IV

Mousse Composition

| Component | Weight % |
|---|---|
| Distilled water | 91.82 |
| Hydrocarbon propellant A-46[1] | 4.80 |
| MEAc/DMA (51%)[2] | 2.86 |
| Alkyl dimethyl amine oxide[3] | 0.24 |
| Glydant preservative[4] | 0.18 |

| Component | Weight % |
|---|---|
| Fragrance | 0.10 |

(1)Propane/isobutane/n-butane (20%/78%/2%) offered by Phillips Petroleum Company
(2)Methoxyethylacrylate/N,N-dimethylacrylamide (49:51) which is prepared as in Example 1 hereinbefore
(3)Cocamine oxide
(4)Offered by Glyco Chemical Company Applying this mousse composition to a person's damp hair and distributing the composition throughout the hair with a comb, followed by letting the hair dry, provides long lasting easy to comb and curl style hold to the treated hair without making the hair feel sticky or stiff.

EXAMPLE V

Synthesis of butylacrylate/methoxyethylacrylate/N,N-dimethylacrylamide (25:25:50)

A 25:25:50 (weight percent) butylacrylate/methoxyethylacrylate/N,N-dimethylacrylamide copolymer is prepared as follows. Butylacrylate, methoxyethylacrylate, and N,N-dimethylacrylamide are weighed out (relative weight ratios of 25:25:50) and added to a three neck flask fitted with an argon sparge, mechanical stirrer and condenser. Toluene is then added to the flask to get a final monomer concentration of 20.0 weight percent. The reaction flask is placed in a 60° C. water bath and the reaction mixture is sparged with argon for two hours while stirring. After two hours, azobisisobutyronitrile ("AIBN") is added to the reaction flask in an amount sufficient to get a final initiator concentration of 0.05 weight percent. The reaction is then stirred for two hours, after which time the reaction flask is removed from the water bath and the reaction mixture is poured into a container of hexane to precipitate the copolymer. The copolymer is then removed from the hexane, placed in a polyethylene tray, and dried in a vacuum oven at 30° C. In order to remove any residual monomer, the dried copolymer is dissolved in toluene, reprecipitated in hexane, and then dried again in a vacuum oven. The glass transition temperature of this copolymer is calculated to be approximately 21° C.

A butylacrylate/butylmethacrylate/N,N-dimethylacrylamide copolymer having monomer content in a weight ratio of 30:30:40 is prepared by following essentially the same procedure. The glass transition temperature is calculated to be approximately 30° C.

EXAMPLE VI

Synthesis of isobutylmethacrylate/2-ethylhexylmethacrylate/N,N-dimethylacrylamide (60:30:10)

A 60:30:10 (weight percent) isobutylmethacrylate/2-ethylhexylmethacrylate/N,N-dimethylacrylamide copolymer is prepared as follows. Isobutylmethacrylate, 2-ethylhexylmethacrylate, and N,N-dimethylacrylamide are weighed out (relative weight ratios of 60:30:10) and added to a four neck flask fitted with an argon sparge, mechanical stirrer, thermometer and condenser. Toluene is then added to the flask to get a final monomer concentration of 25.0 weight percent. The reaction flask is placed in a 60° C. water bath and the reaction mixture is sparged with argon for two hours while stirring. After two hours, azobisisobutyronitrile ("AIBN") is added to the reaction flask in an amount sufficient to get a final initiator concentration of 0.25 weight percent. The reaction is then stirred for two hours, after which time the reaction flask is removed from the water bath and the reaction mixture is poured into a polyethylene tray, air dried, and dried in a vacuum oven at 120° C. (glass transition temperature is calculated to be approximately 38° C.). Optionally, after two hours of stirring, an additional 0.25% initiator is added and the reaction continued for an additional hour, after which time the copolymer is isolated as before. If higher or lower polymer molecular weight is desired, this may be achieved by altering the level of initiator used or by adding a chain transfer agent (such as decanethiol) to the reaction mixture.

An isobutylmethacrylate/2-ethylhexylmethacrylate/N,N-dimethylacrylamide copolymer having monomer content in a weight ratio of 30:40:30 is prepared by following essentially the same procedure. The glass transition temperature is calculated to be approximately 44° C.

EXAMPLE VII

Shampoo Composition

A shampoo composition of the present invention is made by combining the following components.

| Component | Weight % |
|---|---|
| Styling Agent | |
| BMAc/DMA(20%)(1) | 2.00 |
| Orange Terpenes | 6.00 |
| Main Mix | |
| Ammonium lauryl sulfate | 15.00 |
| Jaguar HP-60(2) | 1.00 |
| Kathon CG(3) | 0.03 |
| Perfume | 0.20 |
| DRO H2O(4) | Q.S. |

(1)Butylmethacrylate/N,N-dimethylacrylamide (80:20) which is prepared as in Example 1 hereinbefore.
(2)Hydroxypropyl guar gum offered by Hi-tek Polymers, Inc.
(3)Preservative offered by Rohm and Haas.
(4)Double reverse osmosis water.

The styling agent (premix) is preblended in a conventional manner known to one skilled in the art. The resulting premix resembles an oil. The premix is then dispersed into the main mix by conventional methods including low shear operations such as a propeller stirrer as well as high shear methods such as colloidal milling.

EXAMPLE VIII

Shampoo Composition

A shampoo composition is made by combining the following components.

| Component | Weight % |
|---|---|
| Styling Agent | |
| IBMAc/EHMAc/DMA(60:30:10)(1) | 1.00 |
| 1-Decene | 2.00 |
| Main Mix | |
| Ammonium lauryl sulfate | 10.0 |
| Ammonium laureth sulfate | 6.0 |
| Ethylene glycol distearate | 3.0 |
| Cocamide MEA | 1.00 |
| Kathon CG | 0.03 |
| DRO H2O | Q.S. |

(1)Isobutylmethacrylate/2-ethylhexylmethacrylate/N,N-dimethylacrylamide (60:30:10) which is prepared as in Example VI hereinbefore.

EXAMPLE IX

Shampoo Composition

A shampoo composition is made by combining the following components.

| Component | Weight % |
|---|---|
| Styling Agent | |
| IBMAc/EHMAc/DMA(30:40:30)[1] | 3.00 |
| Cyclomethicone (tetramer) | 9.00 |
| Decyl alcohol | 3.00 |
| Main Mix | |
| Ammonium lauryl sulfate | 11.00 |
| Cocamidopropyl betaine | 4.00 |
| Jaguar HP 60 | 1.10 |
| Kathon CG | 0.03 |
| DRO H$_2$O | Q.S. |

[1]Isobutylmethacrylate/2-ethylhexylmethacrylate/N,N-dimethylacrylamide (30:40:30) which is prepared as in Example VI hereinbefore.

EXAMPLE X

Shampoo Composition

A shampoo composition is made by combining the following components.

| Component | Weight % |
|---|---|
| Styling Agent | |
| IBMAc/EHMAc/DMA(60:30:10)[1] | 0.50 |
| Cyclomethicone (tetramer) | 0.80 |
| Decyl alcohol | 0.20 |
| Premix | |
| Silicone gum[2] | 0.50 |
| Cyclomethicone (tetramer) | 0.60 |
| Main Mix | |
| Ammonium lauryl sulfate | 11.00 |
| Cocamide MEA | 1.50 |
| Xanthan gum | 1.20 |
| Kathon CG | 0.03 |
| DRO H$_2$O | Q.S. |

[1]Isobutylmethacrylate/2-ethylhexylmethacrylate/N,N-dimethylacrylamide (60:30:10) which is prepared as in Example VI hereinbefore.
[2]G.E. Silicone gum SE-76 offered by General Electric.

The styling agent and premix are blended separately and combined with the other ingredients as described above in Example VII.

EXAMPLE XI

Styling Rinse Composition

A styling rinse composition is made by combining the following components.

| Component | Weight % |
|---|---|
| Styling Agent | |
| IBMAc/EHMAc/DMA(60:30:10)[1] | 2.00 |
| 1-Decene | 6.00 |
| Main Mix | |
| Veegum[2] | 1.40 |
| Xanthan gum | 1.40 |
| Cyclomethicone (tetramer) | 0.90 |
| Silicone gum[3] | 0.30 |
| Decyl alcohol | 0.80 |
| Kathon CG | 0.03 |
| DRO H$_2$O | Q.S. |

[1]Isobutylmethacrylate/2-ethylhexylmethacrylate/N,N-dimethylacrylamide (60:30:10) which is prepared as in Example VI hereinbefore.
[2]Magnesium aluminum silicate offered by R.T. Vanderbilt Co.
[3]G.E.S.E. 76

EXAMPLE XII

Conditioner Composition

A conditioner composition is made by combining the following components.

| Component | Weight % |
|---|---|
| Styling Agent | |
| IBMAc/EHMAc/DMA(60:30:10)[1] | 3.00 |
| Phenyl pentamethyl disiloxane | 9.00 |
| Premix | |
| Silicone gum[5] | 0.10 |
| Cyclomethicone (pentamer) | 0.50 |
| Main Mix | |
| Distearyl dimethyl ammonium chloride | 0.85 |
| Natrosol 250M[2] | 0.50 |
| Dow Corning 190[3] | 0.10 |
| Cetyl alcohol | 1.00 |
| Stearyl alcohol | 1.00 |
| Ceteareth-20 | 0.35 |
| Lexamine S-13[4] | 0.50 |
| Perfume | 0.10 |
| Kathon CG | 0.03 |
| DRO H$_2$O | Q.S. |

[1]Isobutylmethacrylate/2-ethylhexylmethacrylate/N,N-dimethylacrylamide (60:30:10) which is prepared as in Example VI hereinbefore.
[2]Hydroxyethylcellulose offered by Hercules, Inc.
[3]A silicone copolyol offered by Dow Corning Corp.
[4]A fatty amine offered by Inolex Chemical Division of American Can Company
[5]G.E.S.E. 76

EXAMPLE XIII

Conditioner Composition

A conditioner composition is made by combining the following components.

| Component | Weight % |
|---|---|
| Styling Agent | |
| IBMAc/EHMAc/DMA(60:30:10)[1] | 0.80 |
| Hexaethyl disiloxane[2] | 2.00 |
| Isocetyl alcohol | 0.05 |
| Main Mix | |
| Stearalkonium chloride | 1.00 |
| Cetrimonium chloride | 0.50 |
| Cetyl alcohol | 1.20 |
| Stearyl alcohol | 0.50 |
| Ceteth-20 | 1.00 |
| Glyceryl monostearate | 0.50 |
| Sodium chloride | 0.05 |
| Kathon CG | 0.03 |
| DRO H$_2$O | Q.S. |

[1]Isobutylmethacrylate/2-ethylhexylmethacrylate/N,N-dimethylacrylamide (60:30:10) which is prepared as in Example VI hereinbefore.
[2]Supplied by Petrarch Chemical

EXAMPLE XIV

Conditioner Composition

A conditioner composition is made by combining the following components.

| Component | Weight % |
|---|---|
| Styling Agent | |
| IBMAc/EHMAc/DMA(30:40:30)[1] | 3.00 |
| D$_4$ cyclomethicone | 6.75 |
| Linalool | 2.25 |
| Premix | |
| D$_5$ cyclomethicone | 1.70 |
| Silicone gum[2] | 0.30 |
| Main Mix | |
| Dow Corning 190 silicone surfactant | 0.50 |

-continued

| Component | Weight % |
|---|---|
| Cetyl alcohol | 0.99 |
| Stearyl alcohol | 0.66 |
| Lexamine S-13[3] | 0.50 |
| Ceteareth-20 | 0.13 |
| Glyceryl monostearate | 0.25 |
| Fragrance | 0.25 |
| Citric acid | 0.90 |
| Kathon CG[4] | 0.04 |
| DRO water | Q.S. |

[1]Isobutylmethacrylate/2-ethylhexylmethacrylate/N,N-dimethylacrylamide (30:40:30) which is prepared as in Example VI hereinbefore.
[2]G.E.S.E. 76
[3]Offered by Inolex Chemical Division of American Can Co.
[4]Offered by Rohm and Haas Company, Inc.

EXAMPLE XV

Hair Tonic Composition

A hair tonic composition is made by combining the following components.

| Component | Weight % |
|---|---|
| MEAc/DMA (51%)[1] | 1.00 |
| Aloe Vera Gel | 2.00 |
| Menthol | 0.06 |
| Citric Acid | 0.04 |
| Perfume | 0.25 |
| SD 40 Alcohol | 35.00 |
| DRO water | Q.S. |

[1]Methoxyethylacrylate/N,N-dimethylacrylamide (49:51) which is prepared as in Example I hereinbefore.

What is claimed is:

1. Hair styling compositions comprising:
(a) from about 0.1% to about 20% of a low glass transition temperature adhesive copolymer which is a random copolymer having the general structure:

$$(H_x)_m\text{---}(L_y)_n$$

wherein:
(A) H is one or more monomer components with relatively high glass transition temperatures, at least one H monomer component being selected from the group consisting of acrylate amides and methacrylate amides;
(B) L is one or more monomer components with relatively low glass transition temperatures, at least one L monomer component being selected from the group consisting of acrylate esters and methacrylate esters;
(C) x and y are integers of 1 or greater, and $x+y$ is an integer of 2 or greater; and
(D) m:n is the weight ratio of H to L monomer components, and the ratio of m:n is within the range of from about 20:1 to about 1:20; and wherein further said adhesive copolymers have a single glass transition temperature within the range of from about 0° C. to about 80° C.; and
(b) from about 80% to about 99.9% of a carrier suitable for applying the adhesive copolymer to hair.

2. Hair styling compositions comprising:
(a) from about 0.1% to about 20% of a low glass transition temperature adhesive copolymer wherein said copolymers is a random copolymer having the general structure:

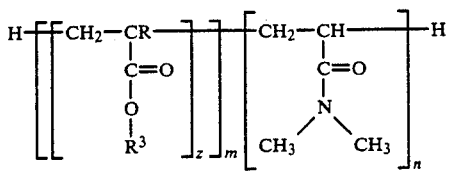

wherein m:n is the weight ratio of the other monomer components to the N,N-dimethylacrylamide monomer component, and the ratio of m:n is within the range of from about 20:1 to about 1:20; z is an integer of 1 or greater; R is selected from hydrogen and methyl; $R^3$ is $C_1$-$C_{15}$ alkyl; and said adhesive copolymers further have a single glass transition temperature within the temperature range of from about 0° C. to about 80° C.; and
(b) from about 80% to about 99.9% of a carrier suitable for applying the adhesive copolymer to hair.

3. Hair styling compositions according to claim 1 wherein at least one of the L monomer components is selected from the group consisting of methylacrylate, ethylacrylate, propylacrylate, butylacrylate, n-butylacrylate, iso-butylmethacrylate, methylmethacrylate, ethylmethacrylate, 2-ethylhexylacrylate, 2-ethylhexylmethacrylate, laurylacrylate, laurylmethacrylate, and methoxyethylacrylate; and at least one of the H monomer components is selected from the group consisting of acrylamide, methacrylamide, N-isopropylacrylamide and N,N-dimethylacrylamide; and $x+y=2$ or 3; and wherein further said adhesive copolymers have a number-average molecular weight in the range of from about 10,000 to about 1,000,000.

4. Hair styling compositions according to claim 3 wherein the ratio of m:n is within the range of from about 10:1 to about 1:10; at least one of the L monomer components is selected from butylacrylate, n-butylacrylate, iso-butylmethacrylate, 2-ethylhexylmethacrylate, and methoxyethylacrylate; and at least one of the H monomer components is N,N-dimethylacrylamide.

5. Hair styling compositions according to claim 2 having a number-average molecular weight in the range of from about 10,000 to about 1,000,000.

6. Hair styling compositions according to claim 5 wherein $R^3$ is selected from the group consisting of methyl, ethyl, n-propyl, iso-propyl, n-butyl, iso-butyl, sec-butyl, tert-butyl, pentyl, 2-ethylhexyl, and —$(CH_2)_2OCH_3$; and z is 1 or 2.

7. Methods for providing styling hold to hair, said methods comprising applying to hair in need of style hold an effective amount of a low glass transition temperature adhesive copolymer according to claim 1.

8. Methods for providing styling hold to hair, said methods comprising applying to hair in need of style hold an effective amount of a low glass transition temperature adhesive copolymer according to claim 3.

9. Methods for providing styling hold to hair, said methods comprising applying to hair in need of style hold an effective amount of a low glass transition temperature adhesive copolymer according to claim 4.

10. Methods for providing styling hold to hair, said methods comprising applying to hair in need of style hold an effective amount of a low glass transition temperature adhesive copolymer according to claim 2.

11. Methods for providing styling hold to hair, said methods comprising applying to hair in need of style hold an effective amount of a low glass transition temperature adhesive copolymer according to claim 5.

12. Methods for providing styling hold to hair, said methods comprising applying to hair in need of style hold an effective amount of a low glass transition temperature adhesive copolymer according to claim 6.

* * * * *